United States Patent [19]
Griffith et al.

[11] Patent Number: 6,088,605
[45] Date of Patent: Jul. 11, 2000

[54] METHOD AND APPARATUS FOR NON-INVASIVE BLOOD GLUCOSE SENSING

[75] Inventors: John S. Griffith, Ebensburg; Patrick J. Cooper, Indiana; Todd Q. Barker, Crafton Heights, all of Pa.

[73] Assignee: Diasense, Inc., Pittsburgh, Pa.

[21] Appl. No.: 09/125,600

[22] PCT Filed: Feb. 21, 1997

[86] PCT No.: PCT/US97/02610

§ 371 Date: Dec. 31, 1998

§ 102(e) Date: Dec. 31, 1998

[87] PCT Pub. No.: WO97/30629

PCT Pub. Date: Aug. 28, 1997

Related U.S. Application Data

[60] Provisional application No. 60/012,305, Feb. 23, 1996.
[51] Int. Cl.$^7$ ..................................................... A61B 5/00
[52] U.S. Cl. .......................................... 600/316; 600/322
[58] Field of Search .................................... 600/310, 316, 600/322, 344, 473, 340

[56] References Cited

U.S. PATENT DOCUMENTS

| 4,655,225 | 4/1987 | Dähne et al. . |
| 5,070,874 | 12/1991 | Barnes et al. . |
| 5,309,907 | 5/1994 | Fang et al. . |
| 5,460,177 | 10/1995 | Purdy et al. . |

FOREIGN PATENT DOCUMENTS

| 0336208 | 10/1989 | European Pat. Off. . |

*Primary Examiner*—Eric F. Winakur
*Attorney, Agent, or Firm*—Webb Ziesenheim Logsdon Orkin & Hanson, P.C.

[57] ABSTRACT

A method and apparatus (12) for the non-invasive sensing of blood glucose levels includes apparatus (10) which moves the forearm of the patient in a controlled incremental manner to take a plurality of spectral skin measurements and averaging the measurements for the purpose of accounting for biological differences that exist in the patient's skin.

8 Claims, 4 Drawing Sheets

METHOD AND APPARATUS FOR NON-INVASIVE BLOOD GLUCOSE SENSING

This application claims benefit of Provisional Application Ser. No. 60/012,305, filed Feb. 23, 1996.

BACKGROUND OF THE INVENTION

1. Field of the Invention

The present invention relates generally to medical diagnostic methods and apparatus and, more particularly, to methods and apparatus for the non-invasive sensing of blood glucose levels.

2. Description of the Prior Art

In the treatment of diabetes, it is oftentimes necessary for the afflicted patient to periodically monitor his or her blood glucose level and then administer appropriate amounts of insulin in response to the glucose level so determined. Heretofore, it has been common to employ a pin prick to the finger in order to draw a blood specimen to determine the glucose level. More recently, non-invasive tests have been developed for this purpose.

It is generally known in the art that radiation, particularly near-infrared radiation over a range of wavelengths, can be projected in a non-invasive manner on a portion of the body of a patient. The resulting radiation emitted from that portion of the body, either scattered or transmitted after absorption and scattering, can be detected and processed to derive an expression of the detected radiation as a function of wavelength and, therefrom, the concentration of blood glucose. Since the detected radiation is a continuous signal covering all of the wavelengths in the range of interest, it is necessary for further analysis to separate the intensities of radiation at the various individual wavelengths, or smaller bands of wavelengths, to extract the desired blood glucose level information.

U.S. Pat. Nos. 5,070,874 and 5,460,177 describe methods for the non-invasive measurement of blood glucose levels. In general, these methods use a spectrophotometer to measure the absorbency of the near-infrared radiation at different wavelengths across the range of interest. The absorbency plotted against the wavelengths constitutes a spectrum. By analyzing the spectrum, the blood glucose levels, or changes thereto, can be determined. As the blood glucose levels vary, the detected spectrum changes slightly.

In order to make the measurements discussed above, the radiation must be transmitted from a radiation source via a sensor head to the skin of a patient and the detected radiation received back from the skin must be collected at the sensor head and carried to a spectrophotometer for further analysis. When making such fine spectral skin measurements, the sensor system measures only a small area of skin which is in intimate contact with the sensor head. Human skin consists of biological components that may be different from point to point over a given area. There may be, for example, certain types of skin cells or hair follicles that vary in composition over a given area of skin. Accordingly, a single, non-invasive measurement of blood glucose level within a given area will vary as greatly as the skin composition itself.

It is an object of the present invention to account for the naturally occurring biological skin variations of a patient so as to permit non-invasive glucose measurement of greatly enhanced reliability and accuracy. It is a further object to provide an apparatus and method which permits self testing by the diabetes patient without the need for specialized clinical assistance.

SUMMARY OF THE INVENTION

Briefly stated, an apparatus according to the invention includes a housing frame for mounting conventional electronic means including a spectrophotometer, electronic control logic and associated hardware for generating and measuring blood glucose by near-infrared radiation. The improved apparatus comprises an arm tray slidably mounted on the housing frame. The arm tray is configured to receive a patient's forearm in a resting mode thereon and position an area of the forearm over a sensor head which is operably coupled to the electronic means of the apparatus. The arm tray is mounted on linear bearings to permit movement of the tray along with the patient's resting forearm in a linear direction along a horizontally extending, longitudinal axis of the patient's forearm. The sensor head is preferably fixed relative to the longitudinal axis of the forearm and extends upwardly through an elongated opening in the arm tray to directly contact the patient's skin when blood glucose sensing measurements are made. A stepper motor rotatably actuates a reciprocating lead screw causing selective linear movement of the arm tray which, in turn, provides controlled movement of the patient's skin relative to the sensor head. One or more blood glucose measurements are made at selected spaced-apart locations along the patient's forearm when the arm tray has stopped. The plurality of measurements is then averaged to obtain a representative blood glucose reading which accurately accounts for biological skin variations occurring over the scanned area.

A further embodiment of the apparatus and method of the invention includes mechanical means for lifting the patient's skin away from contact with the sensor head after a blood glucose measurement is made and movement of the arm tray commences. The skin lifting means comprises a roller mechanism surrounding the sensor head. A linkage and strut assembly carries the roller mechanism and is vertically moveable by a solenoid cylinder. When the solenoid is selectively actuated, at the time when the arm tray is to begin movement, the roller mechanism is raised by the linkage and strut assembly to push the rollers to directly contact and press against the patient's arm. The vertical movement of the roller mechanism is controlled so that the surface of the patient's skin is moved only a small distance from the sensor head surface. The roller mechanism then permits the skin to slide and roll over a spaced-apart pair of rollers as the arm tray moves to reposition the patient's arm at a new skin site for a next blood glucose measurement. Once positioned at the new site, the solenoid is automatically deactivated to lower the linkage assembly and roller mechanism. In this manner, as the roller mechanism drops below the level of the sensor head, the patient's forearm skin is again brought into contact with the sensor head, accurately positioned for the next blood glucose measurement.

These, as well as other attributes and advantages of the present invention, will become more apparent when reference is made to the drawings taken with the following detailed description.

DESCRIPTION OF THE PREFERRED EMBODIMENTS

Figure 1:
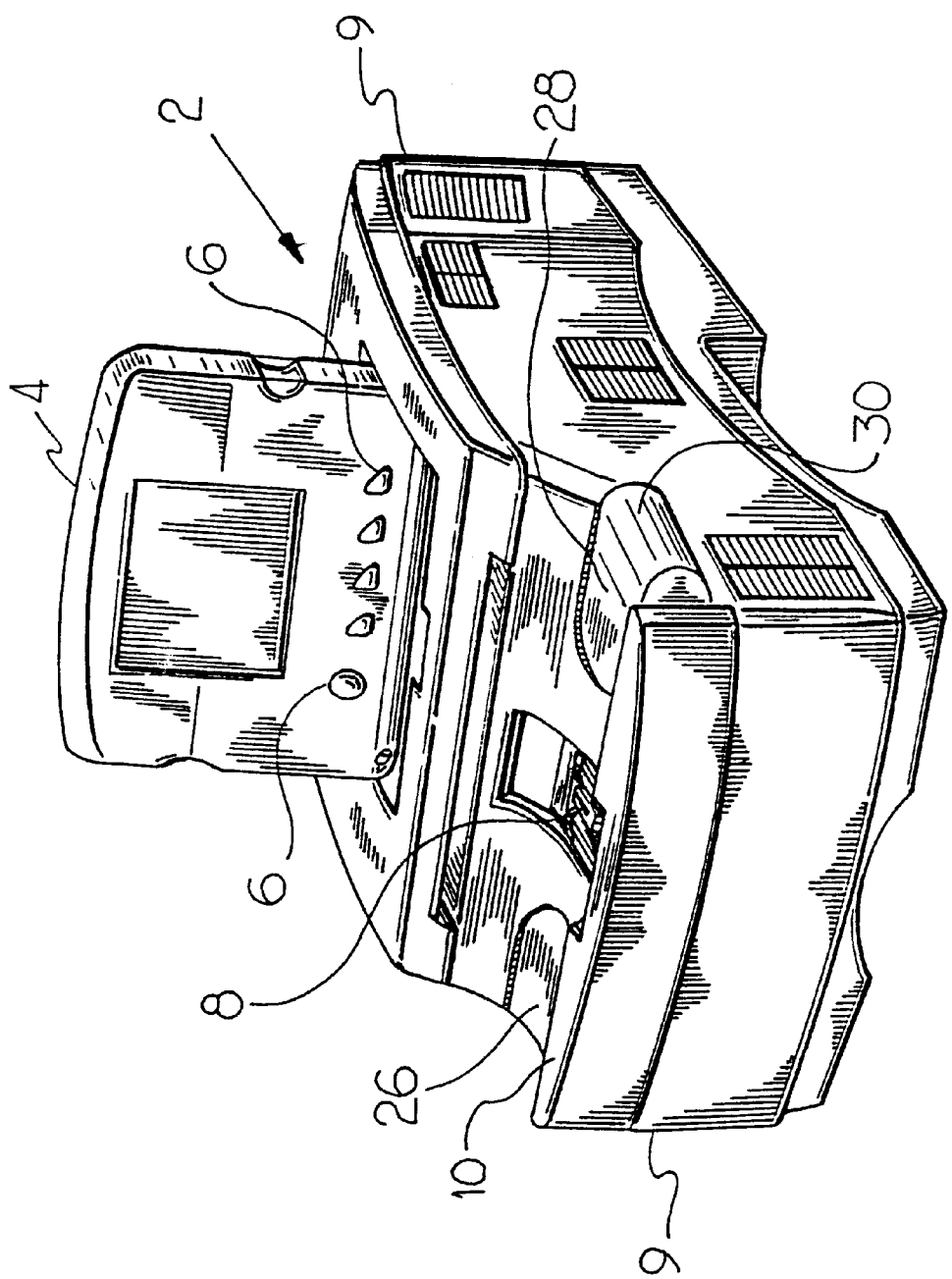
FIG. 1 is a perspective view of a non-invasive blood glucose monitor having a moveable arm tray according to the invention.

A non-invasive blood glucose monitor 2 embodying features of the present invention is depicted in FIG. 1. The blood glucose monitor 2 is a noninvasive diagnostic device which permits a diabetes patient to perform self-monitoring blood glucose measurements so as to maintain proper insulin levels. The monitor 2 includes a screen 4 for displaying blood glucose levels and related information and further includes push button controls 6, or the like, for activation and deactivation of the monitor by the patient. The monitor 2 further includes a sensor head 8 which is intended to make contact with the skin of a patient's forearm situated on the moveable arm tray 10.

The monitor 2 includes an enclosing housing 9 and an underlying support frame 12 for mounting the various electronic means therein, including a spectrophotometer and appropriate electronic control logic and other conventional assorted hardware for generating a near infrared radiation beam at appropriate times and durations. Also included are means for sensing and measuring blood glucose levels based on the amount of radiation sensed. The radiation is transmitted from the sensor head to the underside forearm skin of a patient and the radiation emitted from the patient is transmitted to the spectrophotometer for analysis, all of which is well-known in the art. The present invention concerns the method and apparatus for overcoming biological skin variations which cause significant variations in blood glucose measurements when fine spectral measurements are required.

Figure 2:
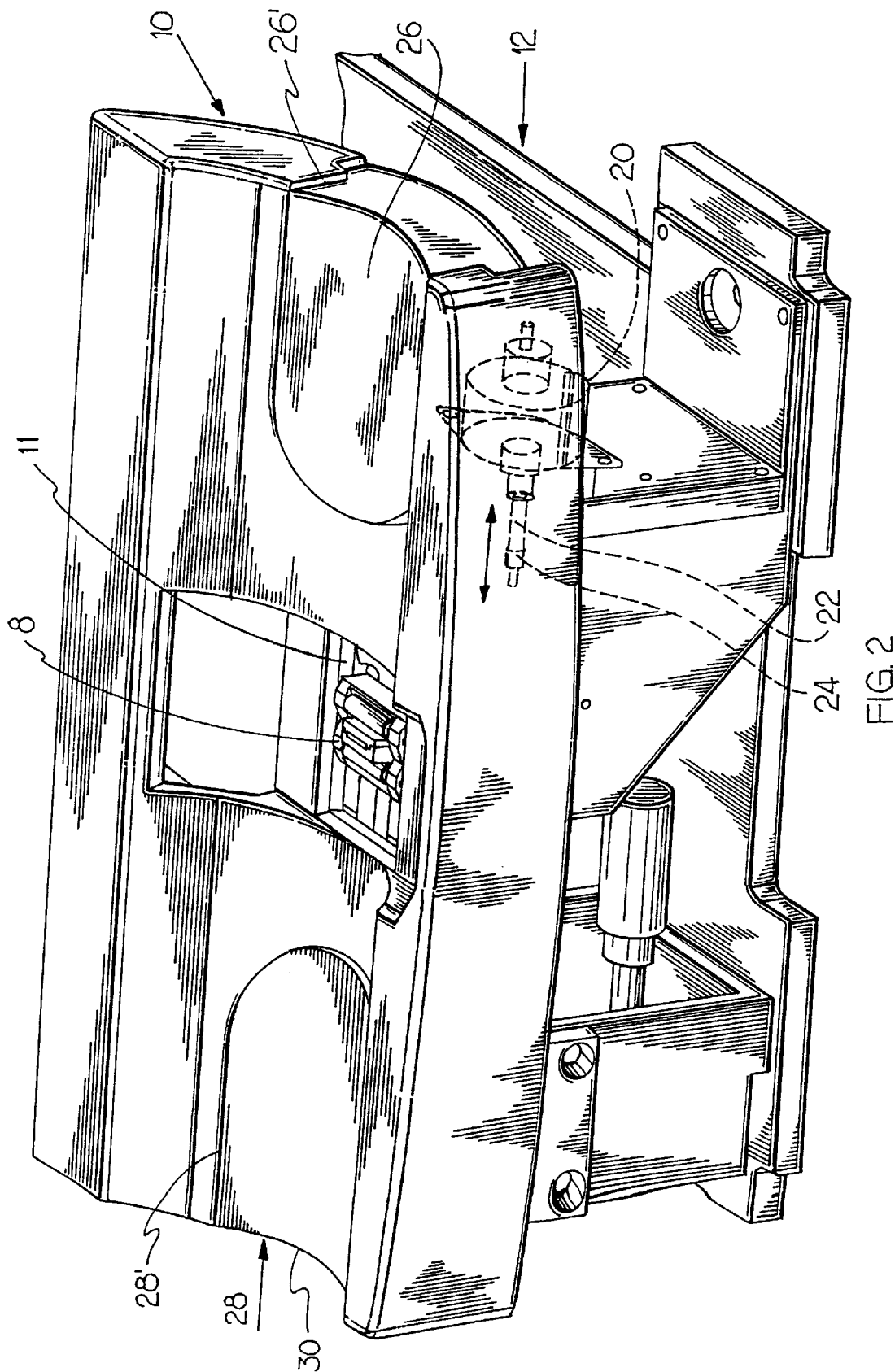
FIG. 2 is a perspective view of the arm tray subassembly of the blood glucose sensor of FIG. 1.
Figure 3:
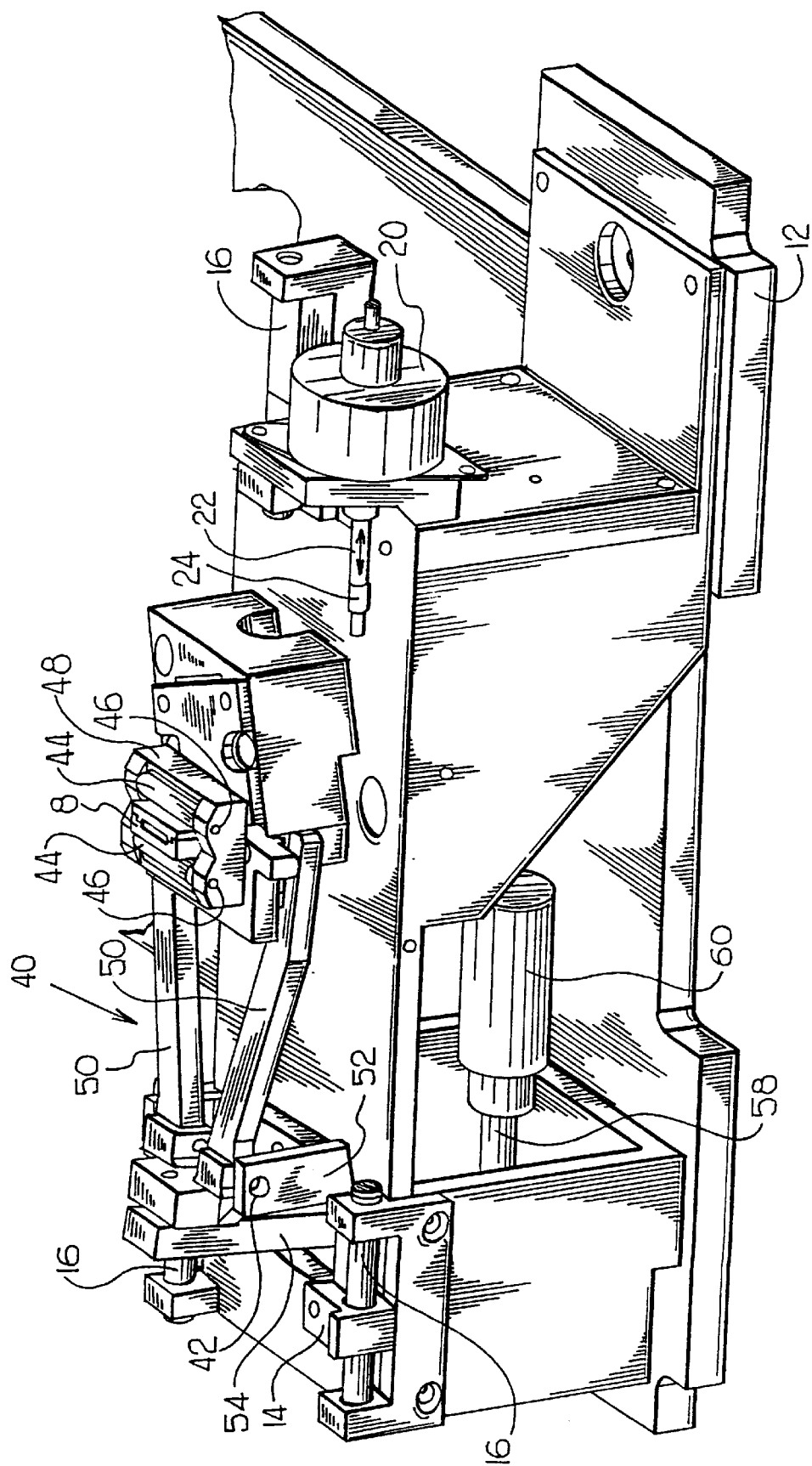
FIG. 3 is a perspective view of the mounting and drive system for the moveable arm tray of FIG. 2.

In order to accomplish this desired objective, the present invention includes a moveable arm tray 10, the details of which are more readily understood with reference to FIGS. 2 and 3. The arm tray 10 is slidable in a horizontal plane relative to the fixed frame 12 of the glucose monitor 2. The arm tray is slidably attached to a plurality of linear bearings 14, one of which is shown in FIG. 3, which travel on fixed bearing shafts 16 carried by the fixed housing frame 12. Preferably, three bearings 14 and shafts 16 are employed. A stepper motor 20 is mounted on the fixed housing frame 12 and carries a reciprocating lead screw 22 which moves inwardly or outwardly when the motor is rotated in one of two directions. The lead screw engages a fixed bracket 24 mounted on the arm tray 10 which then will cause controlled movement of the arm tray when the stepper motor is actuated. Through selection of an appropriate stepper motor and thread pitch of the lead screw, it is possible to control movement of the arm tray 10 in increments as fine as 0.01". Total travel distance of the arm tray along the shaft bearing 16 is preferably between about 3½ to 4".

The arm tray 10 also preferably includes a padded elbow portion 26 and a padded handrest portion 28. The end 30 of the handrest portion serves as a guide or gripping point for the fingers of the patient and functions to position the underside of the patient's forearm over the sensor head 8. The padded portions 26 and 28 are moveable within the grooved guides 26' and 28', respectively, to permit length adjustment to accommodate forearms of various lengths.

The arm tray 10 further includes a cutout portion 11 in a central region thereof to permit the sensor head 8 to directly contact the skin of the patient's forearm. Appropriate control means and logic located in the electronics package of the monitor 2 cause periodic activation of the stepper motor 20 to cause movement of the arm tray relative to the sensor head 8 in a controlled incremental manner so that individual blood glucose measurements can be made in a predetermined array of repeated short and long increments along a longitudinal axis of the patient's forearm, for example, along a total length of 3½". The measurements are then averaged to obtain an accurate glucose measurement which takes into account the variations in the biological components of the skin which may differ from point-to-point over the given measurement field. The movement of the arm tray is adjustable so that the arm movement pattern relative to the sensor head is adjustable and can thus be optimized for each patient.

The arm tray 10 is configured to receive a patient's forearm in a resting mode thereon to position the underside or hairless area of the patient's forearm over the sensor head 8. As previously stated, the sensor head 8 is operably coupled to the electronic means of the apparatus. The arm tray 10 is mounted on the linear bearings 14 to permit smooth and accurate movement of the patient's resting forearm over the sensor head 8 along the longitudinal axis of the forearm. The sensor head 8 is fixed relative to the longitudinal axis of the forearm and extends upwardly through the opening 11 in the tray to directly contact the patient's skin when glucose sensing measurements are made. Activation of the stepper motor activates the lead screw to selectively cause controlled linear movement of the arm tray 10 over an area of the patient's skin to be monitored.

Figure 4:
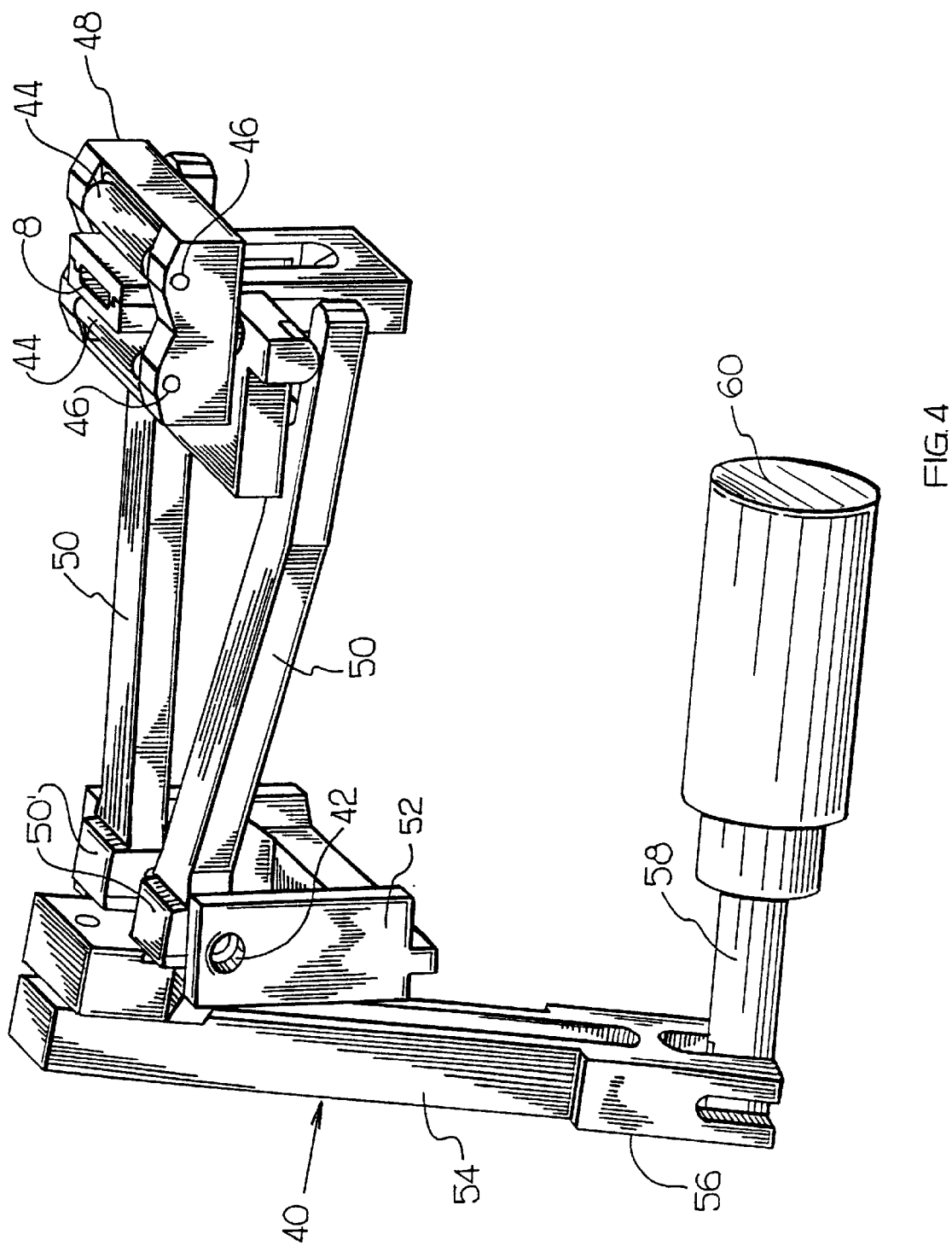
FIG. 4 is a perspective view of a roller and skin lifting mechanism according to the invention for use in the blood glucose sensor of FIG. 1.

The present invention preferably includes a lifting means for moving the patient's skin out of contact with the sensor head as the arm tray is moved. The lifting mechanism is depicted in FIGS. 3 and 4 in greater detail and identified generally by reference numeral 40. The skin lifting mechanism 40 includes a roller assembly comprising two spaced-apart rolls 44 which are rotatable about shafts 46 carried by a support frame 48. The rollers 44 may be, for example, 0.180" in diameter. The roller surfaces make up most of the surface that comes in contact with the patient's skin. However, a small portion of the roller support frame 48 may come in contact with the patient's skin during operation. Hence, the materials of construction are preferably inert and impervious to body acids as well as cleaning solvents used during maintenance of the apparatus. The roller and frame materials preferably employ acetyl plastic as a preferred material of construction. This material provides both inert and non-stick characteristics and provides a good bearing material to accommodate rotation of the rollers 44.

The roller support frame 48 is carried by a linkage system including a pair of struts 50. The struts 50 of the linkage system are pivotally attached at their ends 50' to a stationary yoke 52. A vertical member 54 is attached to the pivoting ends 50' of the struts 50 to move therewith. The lower end 56 of the vertical linkage member 54 is attached to an end of a solenoid shaft 58 which is selectively moved by a solenoid 60. As seen in FIG. 4, inward movement of the solenoid shaft 58 causes the moving portions of the vertical member 54 and the struts 50 of the linkage system to pivot about axis 42. Inward movement of the solenoid shaft 58 thus causes the strut arms 50 to raise the roller support frame 48 and rollers 44 above the level of the sensor head 8. As stated above, the sensor head 8 is fixedly mounted relative to the housing frame 12.

At a time when the arm tray 10 is to begin movement, the solenoid 60 is activated. The roller mechanism 40 is then moved upwardly, as described above, causing the rollers 44 to raise and engage the patient's arm. The vertical movement of the rollers 44 is controlled so as to separate the surface of the patient's skin a small distance from the surface of the sensor head 8. The lifting mechanism then permits the skin to slide and roll over the spaced-apart rollers 44 out of contact with the sensor head as the arm tray 10 moves to reposition the patient's arm to a new skin site for a next measurement. Once positioned at the new location, the solenoid 60 is deactivated to cause an extension of the shaft 58, causing reverse pivotal movement of the skin-lifting mechanism 40 about pivot axis 42 to lower the rollers 44. In this manner, as the rollers 44 drop below the level of the sensor head 8, the patient's forearm skin is again placed in contact with the sensor head 8, thus accurately positioning the sensor head for a next measurement.

While specific embodiments of the invention have been described in detail, it will be appreciated by those skilled in the art that various modifications and alternatives to those details could be developed in light of the overall teachings of the disclosure. For example, while the above-described, presently preferred embodiment of the invention causes the forearm to move relative to a fixed sensor head, of course, the forearm could remain fixed and the sensor head could be moved or, still further, both the sensor head and the forearm could be moved in a controlled manner. Accordingly, the presently preferred embodiments described herein are meant to be illustrative only and not limiting as to the scope of the invention which is to be given the full breadth of the appended claims and any and all equivalents thereof.

What is claimed is:

1. Apparatus for monitoring blood glucose levels in a patient, said apparatus of the non-invasive, near infrared type including a monitor housing having means for generating and measuring near infrared radiation, wherein the improvement comprises:

a) a sensor head operably coupled to the near infrared radiation generating and measuring means for directing and receiving said radiation to and from a patient's skin;

b) an arm tray slidably mounted on said monitor housing adjacent to said sensor head for supporting a forearm of the patient thereon and to position the forearm relative to the sensor head; and c) motive means for incrementally moving and stopping the arm tray relative to the sensor head over a selected distance to permit a plurality of blood glucose measurements to be made along a given area of forearm skin of the patient.

2. The apparatus of claim 1 including means for lifting the skin of the patient away from the sensor head when the arm tray is selectively moved and for returning the skin to a position in contact with the sensor head means when the arm tray is stopped.

3. The apparatus of claim 2 wherein the skin lifting means includes a pair of spaced-apart rollers positioned on opposed sides of the sensor head, said rollers mounted for rotation on a roller support frame, linkage means connected to said roller support frame for raising said rollers to a position above a sensing surface of the sensor head and for lowering said rollers to a position below said sensing surface; and motive means for moving the linkage means to selectively raise and lower the rollers.

4. The apparatus of claim 3 wherein the arm tray has an opening therein to permit the sensor head and skin lifting means to directly contact an underside skin surface of the patient's forearm at selected intervals.

5. The apparatus of claim 1 including hand grip means positioned at an end of the arm tray for grasping by the patient to locate the patient's forearm relative to the sensor head.

6. A method of monitoring a blood glucose level by use of near infrared radiation in a patient comprising the steps of:

a) positioning a sensor head of a blood glucose monitor at a first skin site of the patient;

b) performing at least one blood glucose measurement at said first skin site;

c) repositioning the sensor head to a next skin site and, at the same time, lifting the skin of the patient away from the sensor head;

d) performing at least one blood glucose measurement at said next skin site;

e) repeating steps c) and d) a plurality of times to conduct blood glucose measurements over a given area of skin;

f) averaging the blood glucose measurements made in steps b)–e); and g) releasing the skin to contact the sensor head during steps b) and d).

7. The method of claim 6 wherein the positioning and repositioning steps comprise selective movement of a forearm of the patient relative to the sensor head.

8. The method of claim 6 wherein the skin sites are located on a patient's forearm.

* * * * *